US011141086B2

(12) United States Patent
El Naqa et al.

(10) Patent No.: US 11,141,086 B2
(45) Date of Patent: Oct. 12, 2021

(54) SILICON PHOTOMULTIPLIER ARRAY-BASED MULTISPECTRAL OPTICAL PROBES FOR IMAGE-GUIDED RADIOTHERAPY

(71) Applicant: THE REGENTS OF THE UNIVERSITY OF MICHIGAN, Ann Arbor, MI (US)

(72) Inventors: Issam I. El Naqa, Ann Arbor, MI (US); Ibrahim Oraiqat, Ann Arbor, MI (US); Roy Clarke, Ann Arbor, MI (US); Nicholas Cucinelli, Ann Arbor, MI (US); Samuel Debruin, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 167 days.

(21) Appl. No.: 16/611,687

(22) PCT Filed: May 8, 2018

(86) PCT No.: PCT/US2018/031600
§ 371 (c)(1),
(2) Date: Nov. 7, 2019

(87) PCT Pub. No.: WO2018/208775
PCT Pub. Date: Nov. 15, 2018

(65) Prior Publication Data
US 2020/0107756 A1 Apr. 9, 2020

Related U.S. Application Data

(60) Provisional application No. 62/502,962, filed on May 8, 2017.

(51) Int. Cl.
*G01T 1/20* (2006.01)
*A61B 5/1455* (2006.01)
(Continued)

(52) U.S. Cl.
CPC .......... *A61B 5/1455* (2013.01); *A61B 5/0059* (2013.01); *A61N 5/1067* (2013.01); *G01T 1/2008* (2013.01); *A61B 2562/04* (2013.01)

(58) Field of Classification Search
CPC . A61B 2562/04; A61B 5/0059; A61B 5/0075; A61B 5/0091; A61B 5/1455;
(Continued)

(56) References Cited

U.S. PATENT DOCUMENTS 5,087,818 A 2/1992 Bellian et al.
2004/0238749 A1 12/2004 Fontbonne et al.
(Continued)

FOREIGN PATENT DOCUMENTS

WO WO-2016124083 A1 8/2016
WO WO-2016/176265 A1 11/2016
WO WO-2016210415 A1 12/2016

OTHER PUBLICATIONS

International Search Report and Written Opinion of the International Searching Authority issued in PCT/US2018/031600, dated Aug. 27, 2018; ISA/KR.

*Primary Examiner* — Mark R Gaworecki
(74) *Attorney, Agent, or Firm* — Harness, Dickey & Pierce, P.L.C.

(57) ABSTRACT

Cerenkov Emission (CE) during external beam radiation therapy (EBRT) from a linear accelerator (Linac) has been demonstrated as a useful tool for radiotherapy quality assurance and potentially other applications for online tracking of tumors during treatment. However, an overlooked area is the molecular probing of the cancer status during delivery (Continued)

mainly due to the limited detection sensitivity of CE and lack of flexible tools to fit into an already complex treatment delivery environment. Silicon photomultiplier (SiPM) can be used for low light detection due to their extreme sensitivity that mirrors photomultiplier tubes and yet has a form factor that is similar to silicon photodiodes, allowing for improved flexibility in device design. This work assesses the feasibility of using SiPMs to detect CE, interrogate the tumor molecular status during EBRT, and contrast its performance with silicon photodiodes (PDs) available commercially.

18 Claims, 9 Drawing Sheets

(51) Int. Cl.
  A61B 5/00 (2006.01)
  A61N 5/10 (2006.01)

(58) Field of Classification Search
  CPC ............. A61B 5/4244; A61B 5/4848; A61B 2005/1059; A61N 5/1049; A61N 5/1067; G01T 1/2008
  See application file for complete search history.

(56) References Cited

U.S. PATENT DOCUMENTS

| | | |
|---|---|---|
| 2009/0016399 A1 | 1/2009 | Bowers |
| 2011/0192981 A1 | 8/2011 | Menge et al. |
| 2013/0259339 A1 | 10/2013 | Tian et al. |
| 2014/0114150 A1 | 4/2014 | Pogue et al. |
| 2014/0186967 A1 | 7/2014 | Tsupryk et al. |
| 2015/0338545 A1 | 11/2015 | Arodzero et al. |
| 2016/0263402 A1 | 9/2016 | Zhang et al. |
| 2017/0016766 A1 | 1/2017 | Wijbrans et al. |

SILICON PHOTOMULTIPLIER ARRAY-BASED MULTISPECTRAL OPTICAL PROBES FOR IMAGE-GUIDED RADIOTHERAPY

CROSS-REFERENCE TO RELATED APPLICATIONS

This application is the U.S. National Phase Application under 35 U.S.C. 371 of International Application No. PCT/US2018/031600, filed on May 8, 2018, which claims the benefit of U.S. Provisional Application No. 62/502,962 filed May 8, 2017. The entire disclosures of the applications are incorporated herein by reference.

FIELD

The present disclosure relates generally to optical/radiation probes and, more particularly, to silicon photomultiplier (SiPM) array-based multispectral optical probes for image-guided radiotherapy.

BACKGROUND

Radiotherapy is widely used in the treatment of malignant tumors with more than 60% of all cancer patients receiving ionizing radiation as a main part of their treatment. It is recognized that the efficacy of radiation treatment is highly dependent on the accurate delivery of radiation dose up to the lesion boundary. Currently, evaluating the efficacy of radiation treatment is generally an offline process where radiation technologists use added margins during the planning process and make setup adjustments based on cone-beam computed tomography (CBCT), just prior to radiation delivery of high levels of ionizing radiation to account for inaccuracies in patient placement on the treatment table and internal organ motion uncertainties. Thus, exposing both heterogeneous cancerous and non-cancerous tissues in parallel to high energy ionizing radiation, inadvertently resulting in inefficient tumor cell kill and increased exposure of surrounding vital normal tissue causing inflammatory reactions and other detrimental radiation-related side effects. Therefore, methods for detecting radiation during delivery (i.e., in vivo dosimetry) are needed to improve targeting accuracy and reduce radiation-induced side effects.

Recently, the induction of an intrinsic, internal, optical fluorescent signal during irradiation treatment, known as Cerenkov emission (CE), was shown to be of detectable magnitude for radiation measurement applications, but little has been done to utilize this light for interrogating physiological information.

The information provided in this section is for the purpose of generally presenting the context of the disclosure. Work of the presently named inventors, to the extent it is described in this section, as well as aspects of the description that may not otherwise qualify as prior art at the time of filing, are neither expressly nor impliedly admitted as prior art against the present disclosure.

SUMMARY

This section provides a general summary of the disclosure and is not a comprehensive disclosure of its full scope or all of its features.

In one aspect, a multispectral optical probe is presented. The optical probe includes: a first optical bandpass filter that operates to pass Cerenkov radiation (CE) in a first range of wavelengths; a first silicon photomultiplier (SiPM) photodetector configured to receive radiation passed through the first optical bandpass filter and, in response thereto, generate a first optical response signal; a second optical bandpass filter arranged adjacent to the first optical bandpass filter and operates to pass Cerenkov radiation in a second range of wavelengths, where the first range of wavelengths differ from the second range of wavelengths; and a second silicon SiPM photodetector configured to receive radiation passed through the second optical bandpass filter and, in response thereto, generate a second optical response signal. The first SiPM photodetector and the second SiPM photodetector may be mounted onto a flexible substrate such that the first optical bandpass filter is arranged over top the first SiPM photodetector and the second optical bandpass filter is arranged over top the second SiPM photodetector.

In some embodiments, a scintillator is arranged adjacent to one of the first optical bandpass filter and the second optical bandpass filter and is configured to detect ionizing radiation; and a third SiPM photodetector configured to receive the ionizing radiation and, in response thereto, generate a radiation response signal.

In other embodiments, the flexible substrate is mounted onto a light-blocking pad, where the light-blocking pad is comprised of an opaque material. A transparent barrier may be disposed over top of the first optical bandpass filter and the second optical bandpass filter and coupled along periphery to the light-blocking pad, thereby encasing the first optical bandpass filter, the second optical bandpass filter, the first SiPM photodetector and the second SiPM photodetector.

In another aspect, the multispectral optical probe includes a third SiPM photodetector arranged adjacent to at least one of the first SiPM photodetector or the second SiPM photodetector and, in response to detecting radiation, generates a background signal, where the third SiPM photodetector is covered by a light-blocking material.

The optical probe may further include a fourth SiPM photodetector, where the first, second, third and fourth SiPM photodetectors are arrange in a two-by-two array.

A controller is preferably interfaced with the first SiPM photodetector, the second SiPM photodetector and the third SiPM photodetector, and operates to subtract the background signal from the first optical response signal and the second optical response signal.

In yet another aspect, the multispectral optical probe is integrated into a radiotherapy system. The radiotherapy system includes: a radiation source operates to emit an ionizing radiation beam towards a region of treatment on a subject; and the multispectral optical probe described above. The optical probe may be configured for placement on the region of treatment. A computing device is in data communication with the radiation source and the optical probe. The computing device receives the first optical response signal and the second optical response signal from the optical probe and operates to adjust the ionizing radiation beam based on the first optical response signal and the second optical response signal.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

Figure 1:
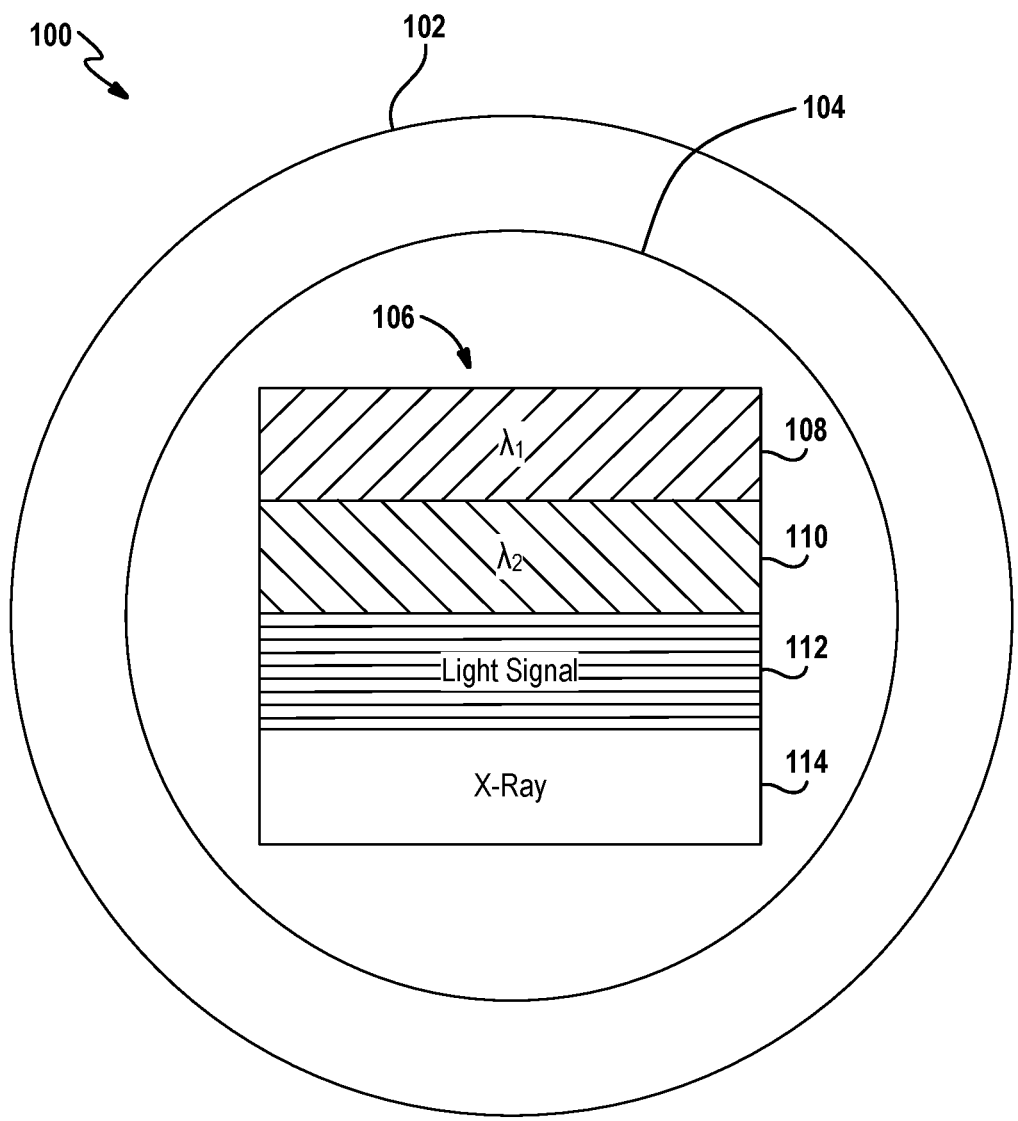
FIG. 1 is a top view of an example optical probe according to the present disclosure.

The induction of an intrinsic, optical emission signal during irradiation treatment, known as Cerenkov Emission (CE) has been shown to be detectable during external beam radiotherapy (EBRT) delivery by linear accelerators (Linacs). CE is generated as visible light when charged particles (electrons) travelling at a speed larger than the phase speed of light polarizes the medium along its track by energy transfer to the surrounding molecules through Coulombic interactions. Subsequently, the electric dipoles created in the medium are de-excited by photon emission. If the particle speed is larger than the phase speed of light, the polarization becomes asymmetric along the particle track because dipoles de-excite more slowly than they are created.

CE has a characteristic spectrum whereby the intensity of the light produced is inversely proportional to the wave length, i.e., primarily in the blue and ultraviolet (UV) part of the electromagnetic spectrum; this results in a low photon count through human tissue due to absorption by hemoglobin circulating the blood, skin melanin, and bilirubin.

Although this phenomenon is well known in the field of radiation physics, its exploitation in cancer imaging is only beginning to happen recently. It has been investigated for potential applications in radiation dosimetry and tracking during radiotherapy. However, the translation of this exciting technology into routine applications in radiotherapy is currently limited by the sensitivity of current photodetectors mainly based on complementary metal-oxide-semiconductor (CMOS) or charge-coupled devices (CCDs) to map radiation dose from Linacs. This is in addition to the complexity associated with installing these detectors into already existing onboard imaging (OBI) radiographic modalities in the treatment room.

Among other features, the present disclosure provides apparatuses, systems, and techniques for utilizing radiation-induced, Cerenkov emission to (1) determine a tumor separating boundary between a cancerous tumor and surrounding normal tissue and (2) characterize tumor aggressiveness by spectrally probing the microenvironment. The present Cerenkov Emission Spectroscopy (CES) approach offers an alternative to conventional radiographic imaging (e.g. low-power x-rays) techniques and their known harmful effects. Improved directional control of a radiation beam with CES may provide a significant paradigm shift in the delivery of radiation therapy for cancer treatment and may reduce dependency on ionizing radiographic imaging. In some examples, the treatment beam itself may be utilized to perform spectroscopic imaging, thus eliminating the need to correlate an image from a different source. Because the Cerenkov signal is of low intensity and is highly attenuated in tissue with a visible spectrum in the blue regions, a new generation of solid-state detectors that have extreme sensitivities with better signal-to-noise ratios may be desired. While the techniques described herein are in the context of treating tumors, it is readily understood that these techniques may be extended to other applications as well.

Silicon photomultiplier (SiPM) solid devices offer low light detection due to their extreme sensitivity that mirrors photomultiplier tubes, yet have a form factor that is similar to silicon photodiodes, allowing for improved flexibility in device design. In some examples of this disclosure, SiPMs (e.g., Sensl MiniSM having 1×1 mm sensor size) are used to detect Cerenkov Emission (CE) during external beam radiation from a linear accelerator (Linac). SiPM photodetectors are solid-state single-photon-sensitive devices built from an avalanche photodiode (APD) array on common silicon substrate. SiPM photodetectors allow for detection of single-photon events in sequentially connected Si APDs.

Referring now to FIG. 1, a top view of an example optical probe 100 according to the present disclosure is provided. The probe 100 may be utilized by itself, or along with other identical or substantially similar probes (see, e.g., FIG. 3) to detect, among other things, a CE signal emitted from a region of treatment that has been the target of an ionizing radiation beam. The CE signal may be utilized to ascertain physiological information such as tumor boundary and aggressiveness, which may be identified through spectral probing of the microenvironment according to the principles set forth herein.

The optical probe 100 is configured to be applied directly to a patient's skin on or around a region of treatment (i.e., a region including one or more cancerous cells). The optical probe 100 may include a light-blocking pad 102, an interfacing substrate 104 disposed on the light-blocking pad 104, and a SiPM photodetector array 106 comprising a plurality of SiPM photodetectors disposed on the interfacing substrate 104. The individual SiPM photodetectors are not directly visible in FIG. 1 because they are positioned under a plurality of photodetector array covering mediums.

For example, a first SiPM photodetector may be disposed beneath a first optical bandpass filter 108, where the first optical bandpass filter operates to pass radiation in a first range of wavelengths $\lambda_1$. A second SiPM photodetector may be disposed beneath a second optical bandpass filter 110, where the second optical bandpass filter operates to pass a second range of wavelengths $\lambda_2$. The first range of wavelengths $\lambda_1$ differs from the second range of wavelengths $\lambda_2$ and preferably are mutually exclusive from each other. A third SiPM photodetector may be disposed beneath a translucent material 112 (labeled "Light Signal" in FIG. 1) and without an associated filter. In some embodiments, a fourth SiPM photodetector may be disposed beneath a scintillator 114 (labeled "X-Ray" in FIG. 1) and configured to detect ionizing radiation associated with a CE signal (e.g., ionizing radiation producing the emission of the CE signal).

Although the SiPM array 106 is shown in a single column arrangement, those having ordinary skill in the art will appreciate that any number of SiPM photodetectors may be included in any suitable arrangement to form the array 106 without departing from the teachings of the present disclosure. For example, in some implementations six SiPM photodetectors arranged in two columns and three rows may be included as part of the array 106. Similarly, any suitable number of (and types of) photodetector array covering media (e.g., optical bandpass filters, scintillators, etc.) may be placed on top of the array 106. The array configuration 106 shown in FIG. 1 is for illustration purposes only and is not intended to limit the present disclosure in any way.

The optical probe 100 may include several layers, with the light-blocking pad 102 forming a base layer, the interfacing substrate 104 forming a layer on top of the light-blocking pad 102, and the array 106 of SiPM photodetectors forming a layer on top of the interfacing substrate 104. The optical bandpass filters 108, 110, translucent material 112, and scintillator 114—collectively—may form a layer on top of the array 106. Additionally, in some implementations, a transparent biological barrier 126 (see FIG. 2) may form a layer on top of the optical bandpass filters 108, 110, translucent material 112, and scintillator 114.

The light-blocking pad 102 may be formed from any suitable opaque material configured to prevent ambient light (e.g., non-CE light present in a room where the patient is undergoing the treatment) from reaching the SiPM photodetector array 106. In one example, a portion of the light-blocking pad 102 (e.g., a portion of the pad on the side facing the interfacing substrate 104) may include adhesive or the like, so that the optical probe 100 may be removably fastened to a patient's skin.

The interfacing substrate 104 may provide mechanical support, as well as an interface, between the SiPM photodetector array 106 and the light-blocking pad 102, and may be formed from any suitable material known in the art. In some examples, the interfacing substrate 104 may be manufactured from a material that does not allow light to pass through, so as to maintain a light-tight environment between the patient's skin and the SiPM photodetector array 106.

The transparent biological barrier 126 (see FIG. 2) may be configured to shield the SiPM photodetector array 106 and other optical probe components from biological contaminants. In some examples, the transparent biological barrier 126 may be removably fastened to the optical bandpass filters 108, 110, translucent material 112, and scintillator 114 by an adhesive. In other examples, the transparent biological barrier 126 seals with the interfacing substrate 104 or the light-blocking pad 102 to create an enclosure for the other components of the optical probe.

Figure 2:
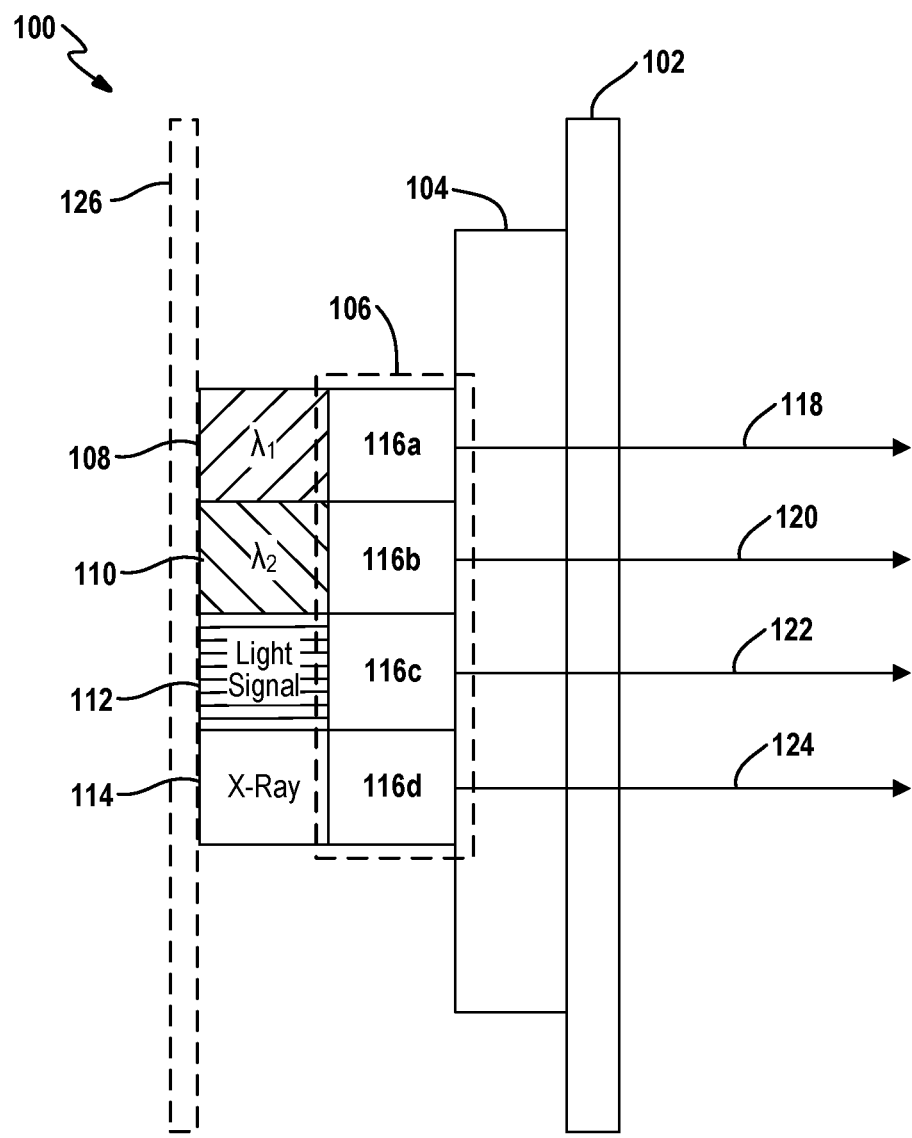
FIG. 2 is a side view of an example optical probe according to the present disclosure.

Turning now to FIG. 2, a side view of the optical probe 100 of FIG. 1 is provided. Notably, FIG. 2 illustrates a plurality of SiPM photodetectors 116a-d that collectively form the SiPM array 106. Although only four SiPM photodetectors 116a-d are shown in FIG. 2, those having ordinary skill will recognize that any suitable number of photodetectors may be included as part of the array 106 without deviating from the teachings herein.

In addition to the SiPM photodetectors 116a-d, FIG. 2 illustrates the optional biological barrier 126 fastened to the optical bandpass filters 108, 110, translucent material 112, and scintillator 114.

Furthermore, FIG. 2 shows a plurality of response signals 118, 120, 122, 124 generated by the SiPM photodetectors 116a-d. In response to receive radiation passed through the first optical bandpass filter, the first SiPM photodetector generates a first optical response signal 118. Likewise, in response to receiving radiation passed through the second optical bandpass filter, the second SiPM photodetector generates a second optical response signal 120. Response signal 122 may constitute an overall intensity response reflecting the intensity of the CE emission across all wavelengths as passed through the translucent material 112. Response signal 124 may constitute a radiation response reflecting the intensity of the ionizing radiation emitted from a radiation beam as detected by the scintillator 114. In some examples, the various responses 118, 120, 122, 124 may constitute electrical signals reflecting the information described above.

Molecular biomarkers of cancer can be measured using Cherenkov Emission (CE) as the predominate excitation source. Optical signals are measured through optical filters and a ratio between various spectral regions is used to quantify spectral intensity changes. This ratio entails one component from the absorbance peak of the biomarker molecule of interest and one (or more) spectral components that do not change with the concentration of the molecule of interest. This leads to a quantitative and normalized measurement that is agnostic to measurement condition changes (this can be extrapolated to any biomarker that can be measured in the UV-VIS-NIR spectral range). Depth changes cause an overall drop in signal intensity. Taking a ratio would normalize this intensity.

Example molecular measurements are described further. For pH measurements, phenol red is injected into patient beforehand and is used as a contrast agent (acid indicator), the ratio between two spectral lines (450 nm and 560 nm) gives the pH in the region of interest. Additionally, taking the ratio of the 560 nm absorbance signal and a spectral measurement outside the range of any absorbance peak will also yield a quantitative pH measurement.

For NAD+/NADH measurements, quantify the amount of NADH by taking the ratio between the absorbance peak of NADH and a spectral region outside of any spectral features as a metric of metabolic activity.

For PO2 (tissue oxygenation), ratiometric measurements of an isosbestic point (spectral point that does not change with PO2) and a absorbance peak that varies with PO2.

For cancer cell targeting, label cancer cells with dye molecule. For example, CE will excite a fluorescence, the optical probe will measure the intensity of absorbance and take a ratio to a spectral feature that is outside of any absorbance (such as NIR). Absorbance from tagged cancer cell will distinguish regions that are cancerous and noncancerous regions. These molecular measurements are merely exemplary of those which can be made using the optical probe described above.

Figure 3:
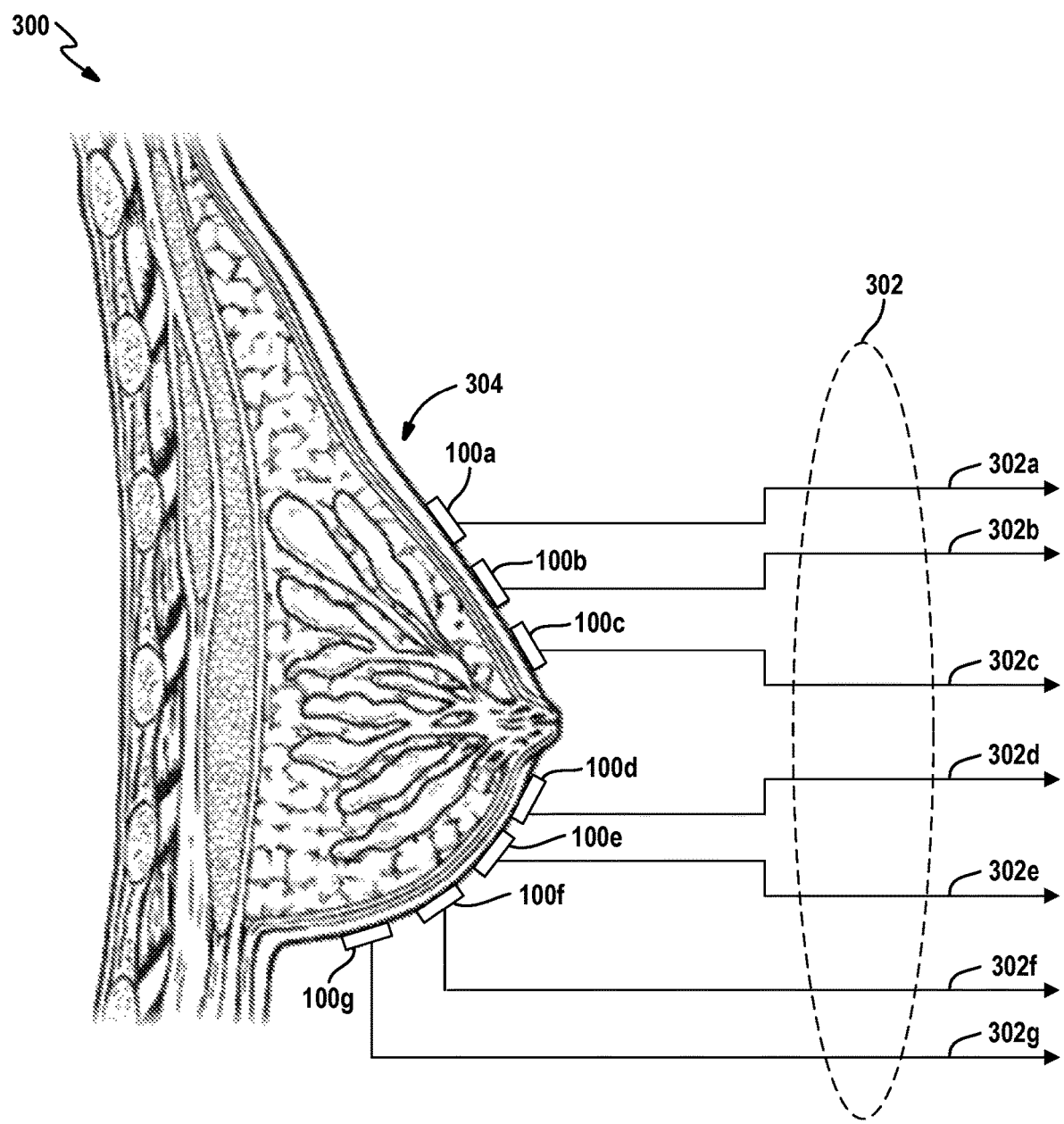
FIG. 3 illustrates a plurality of optical probes disposed on or around a region of treatment according to one example of the present disclosure.

Turning now to FIG. 3, an optical probe system 300 is shown. The optical probe system 300 includes a plurality of discrete optical probes 100a-g disposed on and/or around a region of treatment 304 (in the example shown, a human breast). Upon an ionizing radiation beam being applied to the region of treatment, the affected cells may emit one or more CE signals, which may be detected by the various probes 100a-g according to the properties and techniques discussed above. It is readily understood that different placements and arrangements for the probes depend upon the region of treatment.

Each probe 100a-g is associated with a respective output response signal 302a-g (all of the response signals 302a-g are collectively shown as response signals 302). Although only a single response signal is shown being output from each probe, those having ordinary skill will appreciate that any given response signal (e.g., response signal 302a) may actually include a plurality of response signals, such as the types of response signals 118, 120, 122, 124 discussed above with regard to FIG. 2.

Figure 4:
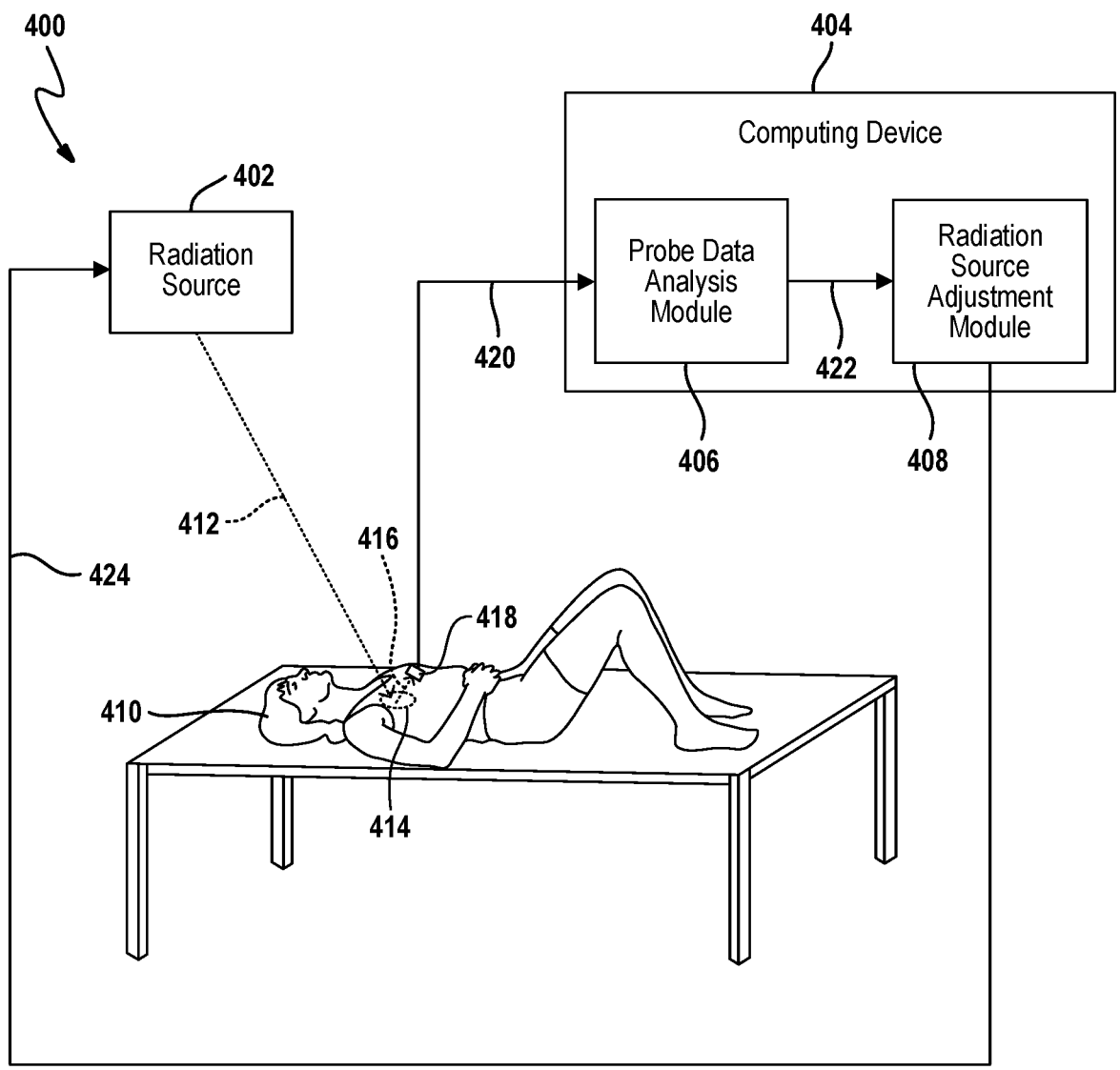
FIG. 4 is a functional block diagram illustrating a system for performing radiotherapy based on CE signal analysis according to one example of the present disclosure.

As discussed in greater detail with regard to FIG. 4, the plurality of response signals 302 may serve as input into a computing device (e.g., the computing device 404 of FIG. 4). The computing device may analyze the response signals 302 from the various probes 100a-g in order to produce a 3D rendering of the treatment area.

In one example, the 3D rendering may include a 3D functional biomarker distribution. In one example, the 3D biomarker distribution may include an internal 3D map of pH and/or tissue oxygenation. In some examples, this information may be utilized to identify tumor aggressiveness (because tumors are heterogeneous) with respect to the radiation dose being applied. For example, a radiation dose may be increased in a sub-region identified to have increased cancer aggressiveness. Conversely, a radiation dose may be decreased in a sub-region associated with less aggressive (or no) cancer. Accordingly, the probes 300a-g of system 300 disclosed herein may be utilized to adjust radiation dosage strength to optimally combat cancer. In addition, as discussed below, the probes may also be utilized to adjust the direction of the ionizing radiation beam to focus on cancerous cells and avoid healthy cells.

Turning now to FIG. 4, one example of a system 400 for performing radiotherapy based on CE signal analysis is shown. The system 400 includes a radiation source 402, one or more optical probes 418 (each including an array of SiPM photodetectors) affixed to a patient 410, and a computing device 404 operatively connected (e.g., via one or more wired or wireless communication channels) to both the probe(s) 418 and the radiation source 402.

In operation, the system 400 functions as follows. The radiation source 402 is configured to transmit an ionizing radiation beam 412 at a region of treatment 414 on the patient 410. The ionizing radiation beam 412 may cause tissue in the region of treatment 414 to emit one or more CE signals 416. The one or more probes 418 are configured to detect the one or more CE signals 416. For example, the one or more CE signals 416 may be detected by an array of SiPM photodetectors connected to respective optical bandpass filters.

In addition, the one or more probes 418 are configured to detect ionizing radiation from the ionizing radiation beam 412 in the region of treatment 414. For example, the ionizing radiation may be detected by one or more SiPM photodetectors (of an array of SiPM photodetectors) connected to one or more respective scintillators. In some examples, the one or more probes 418 may be further configured to detect all wavelengths of a CE signal. For examples, the wavelengths of a CE signal may be detected by at least one SiPM photodetector connected to a translucent material.

Furthermore, the one or more probes 418 may be configured to generate response signals 420 characterizing the CE signal 416 and the ionizing radiation. The response signals may be transmitted to the computing device 404 for processing (e.g., amplification) and/or analysis. As used herein, the computing device 404 may comprise one or more processors and memory storing executable instructions capable of execution by the processor. In one example, the computing device 404 may include a probe data analysis module 406 and a radiation source adjustment module 408.

The probe data analysis 406 module may be configured to analyze the response signals 420 to determine physiological information about the tissue cells in the region of treatment. For example, a ratio between a first spectral intensity associated with a first SiPM photodetector connected to a first optical bandpass filter and a second spectral intensity associated with second SiPM photodetector connected to a second optical bandpass filter may be determined by the probe data analysis module 406 to characterize a given cell (or collection of cells) as cancerous versus non-cancerous cells. In addition, in some examples, the probe data analysis module 406 is configured to analyze the response signals 420 to determine a level of aggressiveness of identified cancer cells based on, for example, detectable oxygen/pH differences between various cells.

The probe data analysis module 406 is configured to generate analysis data 422, which may be transmitted to the radiation source adjustment module 408. The radiation source adjustment module 408 may be configured to generate instructions 424 to the radiation source 402 so as to adjust parameters of the radiation source 402. In one example, the probe data analysis module 406 is configured to generate an instruction to adjust (e.g., increase or decrease) a dosage, or intensity, of the ionizing radiation beam 412. As noted above, the dosage, or intensity, of the ionizing radiation beam 412 may be adjusted, in some examples, based on the aggressiveness of any identified cancer cells. In another example, the probe data analysis module 406 is configured to generate an instruction to adjust a direction of the ionizing radiation beam 412. As noted above, in some examples, the direction of the ionizing radiation beam 412 may be adjusted to ensure that the beam 412 targets cancerous cells and avoids healthy cells.

Figure 5:
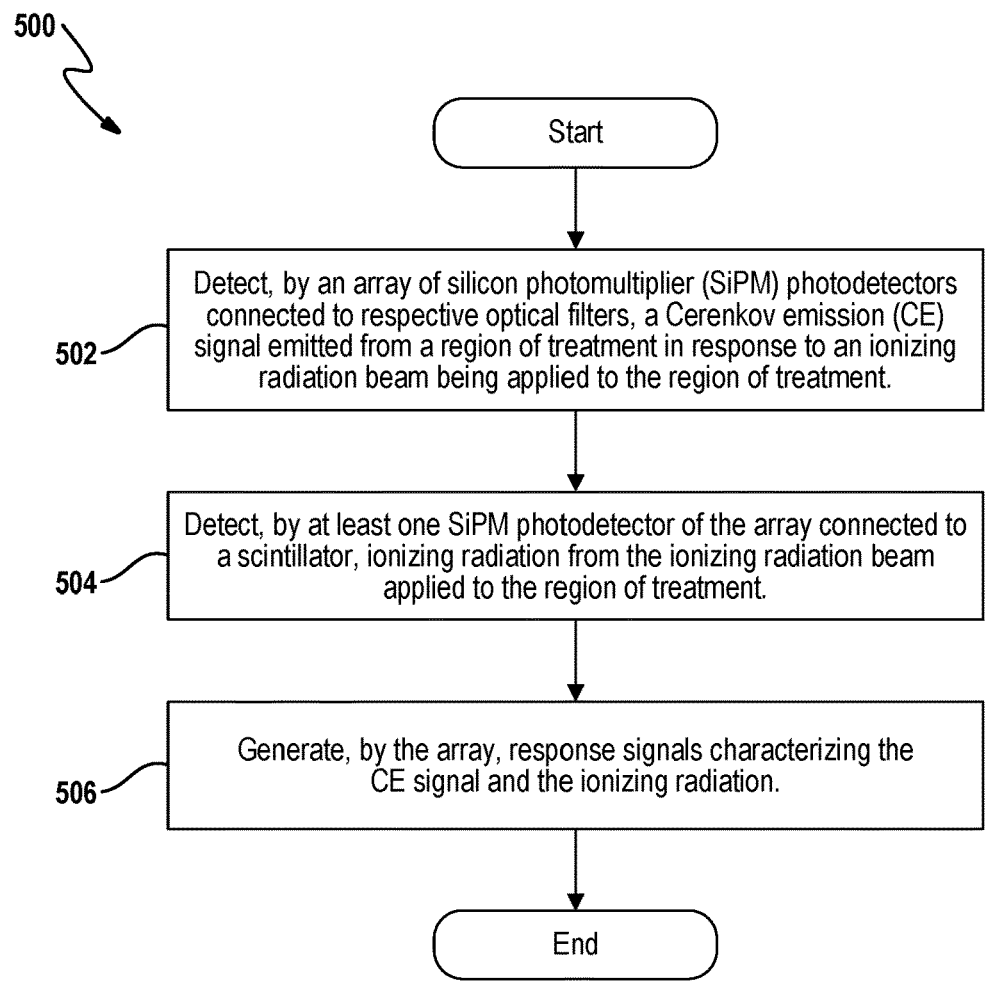
FIG. 5 is a flow diagram illustrating a method for performing radiotherapy based on CE signal analysis according to one example of the present disclosure.

Referring now to FIG. 5, a flowchart of a method 500 for performing radiotherapy based on CE signal analysis is shown. The method 500 begins at 502 where a CE signal emitted from a region of treatment is detected in response to an ionizing radiation beam being applied to the region of interest. The detection may be accomplished by an array of SiPM photodetectors connected to respective optical bandpass filters.

At 504, ionizing radiation is detected from the ionizing radiation beam applied to the region of treatment. The detection may be accomplished by at least one SiPM photodetector of the array connected to a scintillator.

At 506, response signals are generated that characterize the CE signal and the ionizing radiation. The response signals may be generated by the array of SiPM photodetectors. Following 506, the method concludes.

Figure 6:
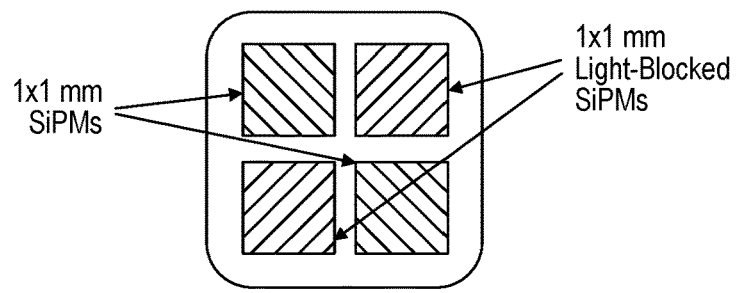
FIG. 6 is a schematic of SiPM pixel arrangement, showing two channels that are blocked out to optical light to aid distinguish optical signals from scattered x-ray signals and background correction.

As proof of concept, a 4 mm (active area) probe was designed around four 1 mm SiPMs (SensL, Dublin, Ireland) pixels as seen in FIG. 6. Each pixel corresponds to a single channel. The pixels are mounted onto a flexible substrate and covered by a transparent barrier. The transparent barrier preferably seals with the flexible substrate. The flexible substrate may be designed for elasticity and proper impedance. In an example embodiment, the flexible probe is a single circuit board incorporating three distinct zones. There are two rigid zones (i.e., the probe zone containing the SiPM sensors and the connection zone containing the high-density board-to-board connector) connected by a long flexible zone. In the PCB stackup, the flexible electrical/conductive layers run throughout all three zones, but there is a rigid stiffener backing in the rigid zones. Specifically, the cross section of the flexible/cable section is as follows: (cross section): 1 mil polyimide, 1 mil adhesive, 1 oz copper, 4 mil polyamide, 1 oz copper, 1 mil adhesive, and 1 mil polyimide. In the rigid section, on the bottom of the stackup is an additional rigid layer: 40 mil with 3M467 pressure sensitive adhesive (PSA). The thickness of the copper layer, flexible polyamide and adhesive layer are optimized for flexibility and strength while maintaining a consistent 50 ohm transmission. Other types of materials and constructs are contemplated by this disclosure.

On the bottom of the probe is a connector for a flat-flexible ribbon cable, which supplies power to the probe and carries the signal from each SiPM pixel. The probe is 6 mm wide, 5 mm long, and 1.5 mm thick. The flexible cable is 3.7 mm wide and can be up to 25 cm long.

At the other end of the flexible cable is the controller, which generates power for the probe and amplifies the return signals. The four pixels on the probe are negatively biased at approximately −29 V. The bias voltage is configurable through a custom-made controller circuit to adjust for specific conditions. The probe itself contains conditioning circuitry for the bias voltage. The four signals from the probe are DC coupled to the controller, which contains an integrated transimpedance amplifier with a nominal amplification of 2,200 V/A.

In this example embodiment, two SiPM pixels are covered in light blocking material while the other two are left as open pixels for light detection. The reason for this is to distinguish optical signals from scattered x-ray signals and stem effects (i.e., CE induced in any extra material on top of the SiPM, such as a transparent plastic food wrap to act as a biological barrier between the probe and phantom). Data acquisition is gated to the Linac target trigger and signals from all four channels are collected simultaneously, for example using an oscilloscope (GW Instek GDS-3504); this collected signal is from a single Linac pulse. The oscilloscope transfers data to a computer for further processing. The difference is taken between one open pixel and an adjacent light-blocked pixel. This difference yields the optical signal that is purely from the CE of the phantom during a single Linac pulse, removing any signals that results from direct x-rays and signals that may result from CE from any media associated with the probe (i.e., background stem effect). The choice of which adjacent pixel is light-blocked depends on the geometry of the measurement. For example, if measurements are taken horizontally (such as looking at a horizontal gradient of CE intensity), the adjacent light-blocked blocked pixel should be vertical from the open light detection pixel, keeping them on the same plane with respect to the signal gradient.

In an alternative embodiment, the four pixels are configured differently. For example, one pixel is a scintillator, one pixel is covered in light blocking material and the other two pixels are for light detection. Other arrangements and combination of pixel functions are contemplated by this disclosure.

For all measurements, the entire set-up (including phantoms) is wrapped in a light blocking fabric (e.g., ThorLabs BK5 black rubberized plastic) and the treatment room lights are turned off to reduce any background optical signals. Data acquisition is gated to individual Linac pulses by triggering the oscilloscope to the target output (which is the current generated when electrons strike the tungsten target to produce 6 MV x-rays) of the Linac. Each trace is an average of 16 traces from individual Linac pulses. The amplitude is measured of this averaged trace using the onboard oscilloscope amplitude measurement algorithms. A total of 128 amplitude measurements are collected and averaged. All data for subsequent experiments, unless otherwise noted, are acquired in this fashion.

CE was stimulated using 6 MV photons generated in a Linac (Varian TrueBeam™) and measured using the SiPM probes that are gated to the Linac target trigger. Instantaneous dose is defined here as the dose delivered during an individual Linac pulse. The signal pulse height (in V) from the SiPM probe is proportional to the intensity of CE during that pulse, which is in turn proportional to dose.

Figure 7:
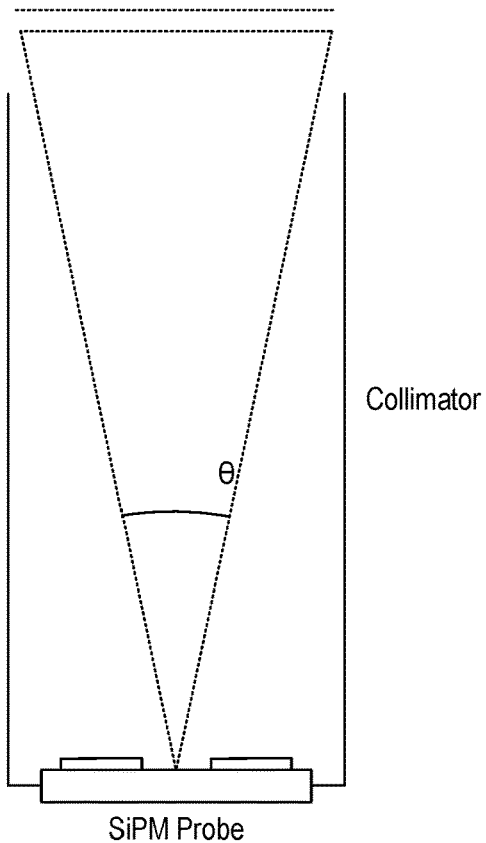
FIG. 7 is a schematic of the collimator interfaced with the optical probe to reduce the solid angle of detection to $0$-$0.012\pi$ steradian.
Figure 8:
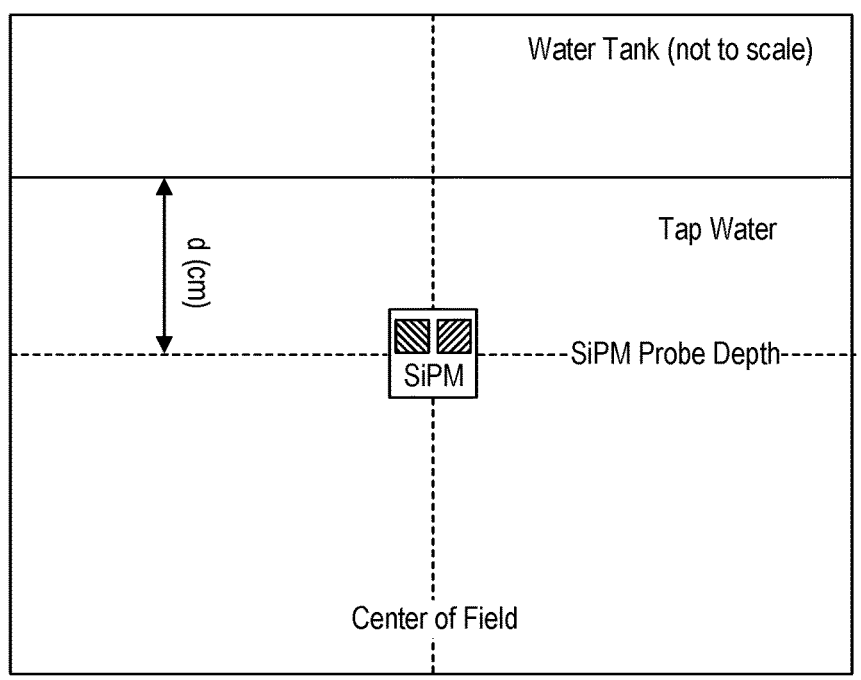
FIG. 8 is a side view of the experimental setup, where optical probes are aligned so they are at a constant depth from the water surface (10 cm)

Initially, measurements of CE intensity versus depth inside a water tank were taken to generate percent depth dose (PDD) curves using the SiPM optical probes at 6 MV. The water tank is setup at 95 cm SSD. Ion chamber PDD measurements in water tank were originally taken at 100 cm SSD during commissioning, and the PDD was converted to 95 cm SSD. The edge of a 3×3 cm field is placed 1 cm from the SiPM probe at isocenter. A light collimator, which consists of a black hollow tube with a length of 2.54 cm and an inner diameter of 0.66 cm, is attached to the SiPM probe to reduce the solid angle of detection for the probe from $2\pi$ steradian to approximately $0.012\pi$ steradian as seen in FIG. 7. The SiPM probe is taped onto the outside of a transparent water tank at various depths as measured from the center of the top two pixels of the probe to the water surface, as shown schematically in FIG. 8. The depth range is measured from 0 cm to 20 cm, with 0.5 cm intervals until a depth of 5 cm, followed by an interval of 1 cm until 20 cm. Due to the divergence of the radiation beam, the sensor to field's edge distance is not equal to 1 cm at every position that is off isocenter; therefore, a correction factor as a function of tank depth is applied for each depth point using similar triangles and inverse-square law.

Figure 9:
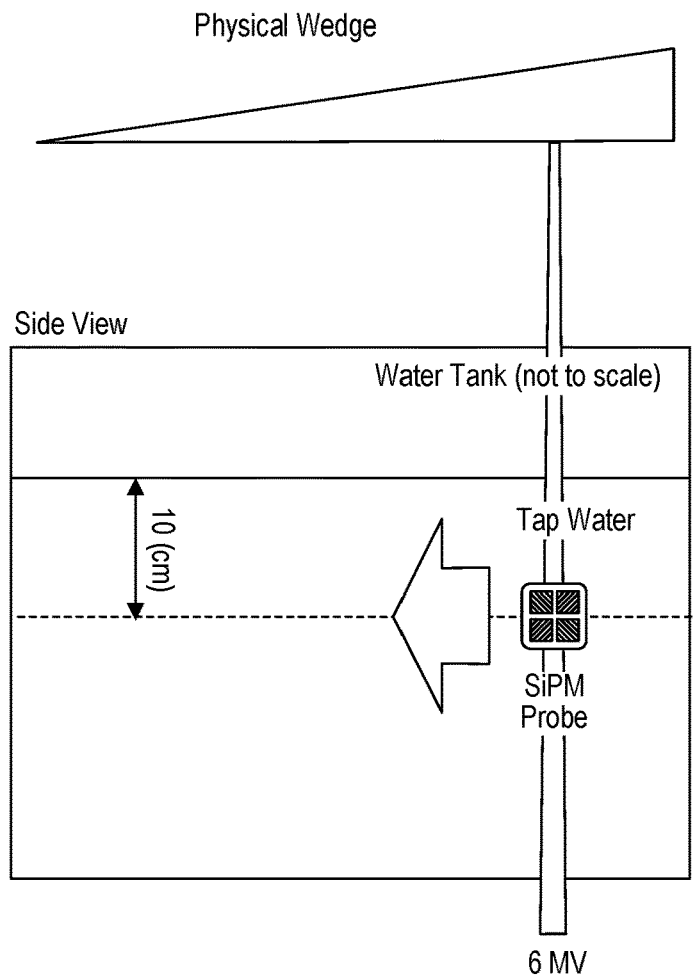
FIG. 9 is a side view of the experimental setup, where the optical probes are aligned such as they are at a constant depth from the water surface (10 cm), a 0.5×1 cm 6 MV field is scanned across the physical wedge (30° and 60°) while the optical probe is repositioned to track the field.

Next, the ability to measure gradients in the radiation field by discerning changes in CE intensity during each Linac pulse is assessed. A small rectangular field size of 0.5×1 cm is used, where the 0.5 cm is the width of the field from the SiPM probe perspective. A gradient is introduced by using 60° and 30° physical wedges which are subsequently attached to the head of the Linac. The optical phantom consists of a water tank filled with municipal tap water. As shown schematically in FIG. 9, the center of the SiPM optical probe is attached to the outside of the tank and is aligned at 100 cm source to axis distance (SAD) with a water depth of 10 cm, corresponding to 90 cm source to surface distance (SSD). The field is then scanned across the wedge in a "step and shoot" fashion by adjusting the collimator jaw positions asymmetrically on the Linac. The probe position and the field stay fixed with respect to each other by adjusting the treatment couch position to move the relative probe position; since the water tank is perturbed due to couch movement, the water is given 60 seconds to settle. Since measurements are taken along a gradient in the horizontal axis, the light-blocked pixels are chosen to be below the open pixels for applying real time stem effect and stray radiation corrections (on the order of 5%).

Film dosimetry was used as a benchmark to compare the CE measurements. Radiochromic film was sandwiched between blocks of water equivalent plastic, with 10 cm of solid water on top of the film, which is placed at 100 SAD to simulate the experimental conditions used for CE measurements. The film was irradiated with 2 Gy along the beam central axis with a 15×15 cm 6 MV field.

A photodiode system is used as a benchmark comparison for the SiPM probe, which consists of a commercial mounted silicon photodiode (Thorlabs FD11A), DC Bias Module (Thorlabs PBM42), and a transimpedance amplifier (Texas Instruments OPA659) adjusted to have the same nominal amplification as what is used for the SiPM probes (2,200 V/A). The signal is acquired using the same oscilloscope (GW Instek GDS-3504) as the SiPM Probes. To simulate a soft tissue scenario, a phantom consisting of ground pork with a fat content of 31.1% vol is used. Ground pork is placed into a 10×10×10 cm black painted acrylic box (with a thickness of 3 mm) and shaped to the geometry of the box. The top of the box is open with the ground pork flattened at the same level as the box, as seen on the top of FIG. 9. A clear polyethylene food wrap (Saran wrap) is wrapped around the probe to act as a protective barrier between the SiPM/photodiode probe that is placed on top of the ground pork phantom.

Figure 10:
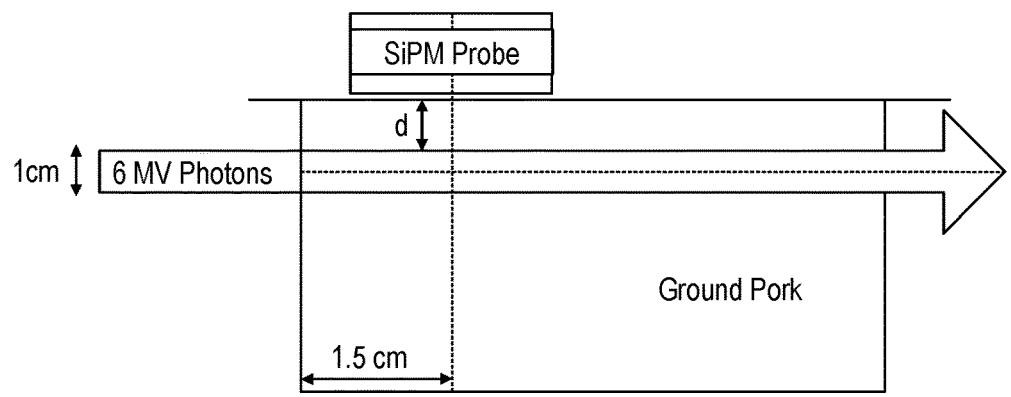
FIG. 10 is a schematic of the ground pork phantom, where "d" is the distance between the edge of the pork phantom and the distance between the center of the probe and the edge of the phantom is 1.5 cm.

FIG. 10 shows a schematic of the experimental setup. CE from a 1×3 cm 6 MV field is measured at various depths in the ground pork phantom, which is varied by adjusting the height of the treatment couch. Depth, d, is defined as the distance from the top edge of the field to the SiPM/photodiode. The probes are placed at a distance of 100 cm SAD with a position 1.5 cm from the entrance side of the radiation field for maximum buildup of radiation dose. Measurements taken with black-out cloth material wrapped around the probes are subtracted from the overall measured signals at each depth to account for any CE originating from the polyethylene food wrap.

Figure 11A:
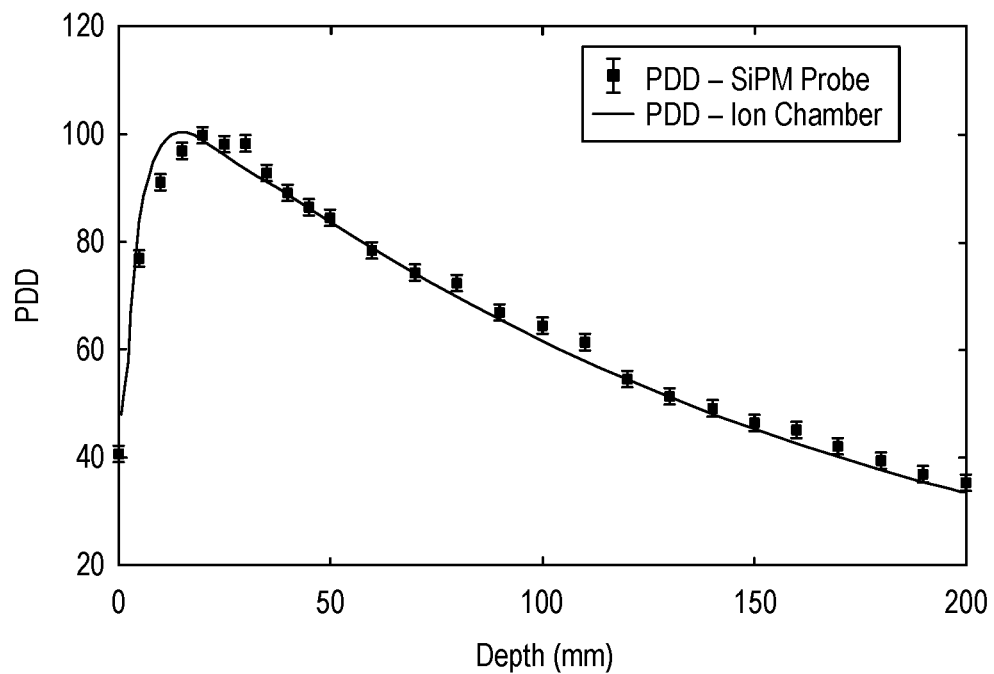
FIG. 11A is a graph of normalized signal strength compared to the PDD measurements generated by scanning an ion chamber in a water tank for this linear accelerator (Linac) during is commissioning.
Figure 11B:
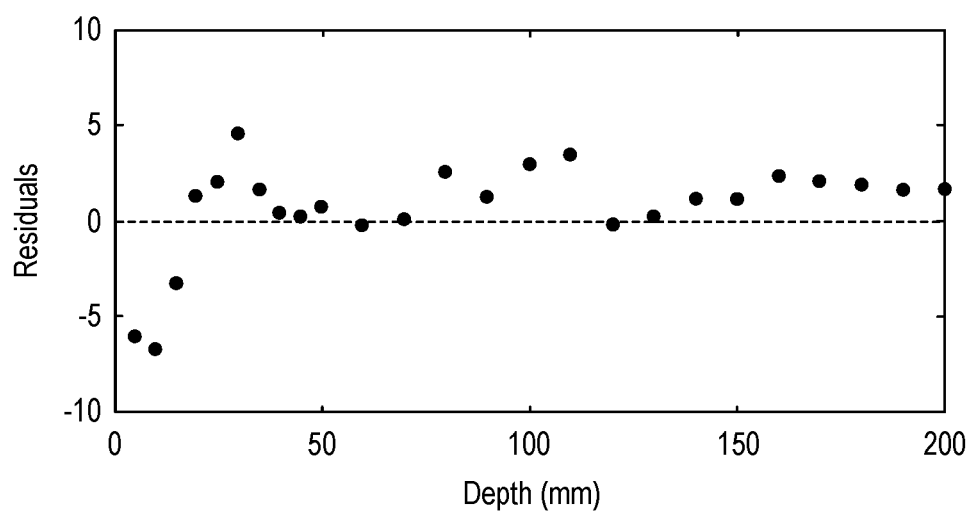
FIG. 11B is a graph of a residual plot comparing the optical probe measured PDD data and the expected values collected during Linac commissioning.

FIG. 11 shows a comparison between PDD data taken using the SiPM probe and the ion chamber from water tank scans during commissioning of the same Linac used in these experiments. Qualitatively, the data from the SiPM does show a buildup region followed by a fall off region, as expected from a MV photon field. When compared with the commissioning data, it is apparent that there is a slight shift in the maximum dose position (2 cm vs 1.5 cm) while the SiPM data tracks the commissioning well in the fall off region, the overall root mean square error is 2.6 (in units of PDD). This uncertainty can be attributed to a possible acquisition error at the point of measurement due to probe misplacement and refraction from various optical interfaces between the SiPM and the radiation field. Since the slope is changing drastically in the build-up region, these errors are relatively exacerbated, which can be seen in the residual plot in FIG. 11B.

Figure 12:
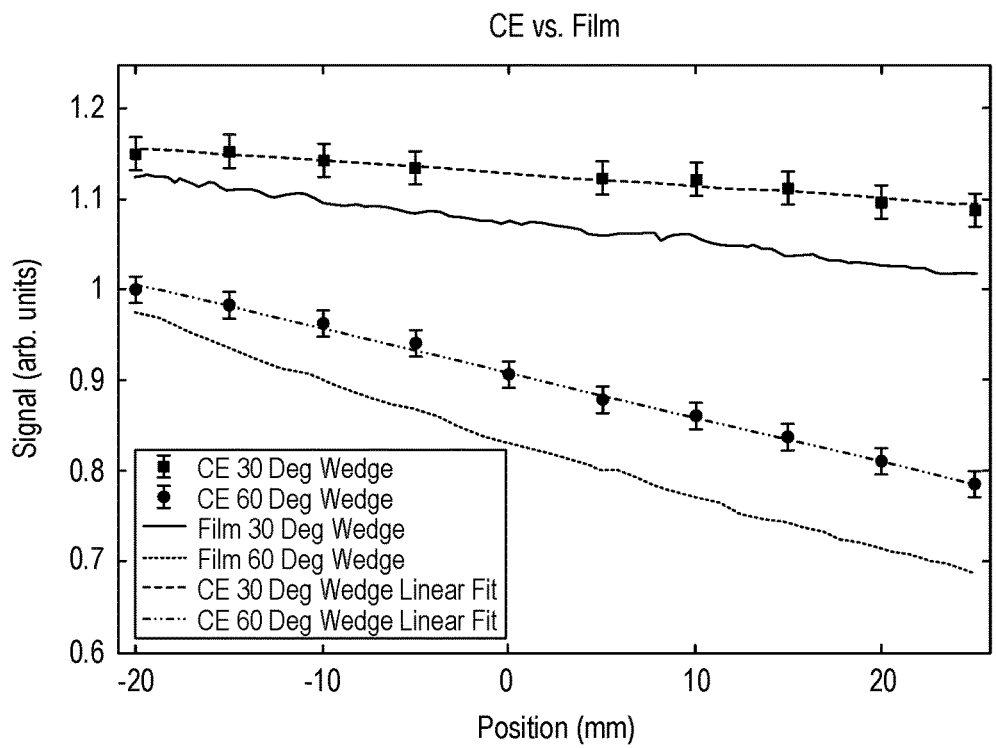
FIG. 12 is a graph showing signals from the optical probe (dashed lines) corresponding CE from a 0.5×1 cm 6 MV photon field delivered using a Linac at different lateral positions with 30 and 60 degree wedges compared to corresponding radiochromic film measurements (solid lines)

FIG. 12 shows CE intensity measured using the SiPM probe as a function of position for 30° and 60° physical wedges. A linear regression is used to determine the slope of each wedge measurement. For the 30° wedge, the slope (in arbitrary units per mm) is $-1.386 \times 10^{-3}$ ($R^2=0.9496$) and $-4.882 \times 10^{-3}$ ($R^2=0.9951$) for the 60° wedge, showing a steeper slope for the 60° wedge.

Radiochromic film measurements were again used as a comparison. The center of the film was normalized to arbitrary units and compared with the CE measurements. Qualitatively, the CE measurements match with the film measurements (i.e., the slopes are steeper for the 60° wedge vs the 30° wedge). There is deviation between the slopes of the film measurements, $-2.389 \times 10^{-3}$ vs $-1.386 \times 10^{-3}$ (a ratio of 1.72) and $-6.360 \times 10^{-3}$ vs $-4.882 \times 10^{-3}$ (a ratio of 1.30) for the 30° and 60° wedge, respectively. Although the trends are consistent, however, there are deviations that can be attributed to two sources. The first and most prominent source is that the measurements with the SiPM probe are taken with an aperture averaging technique. From the perspective of the probe, the field is 0.5 cm; since there is a physical wedge, the output signal from the probe is the integration of the signal over that gradient. The other source of deviation may be due to slightly different film measurement conditions compared to the CE measurements. Film measurements were taken using a continuous field whereas the probe measurements are taken at discrete points.

Figure 13:
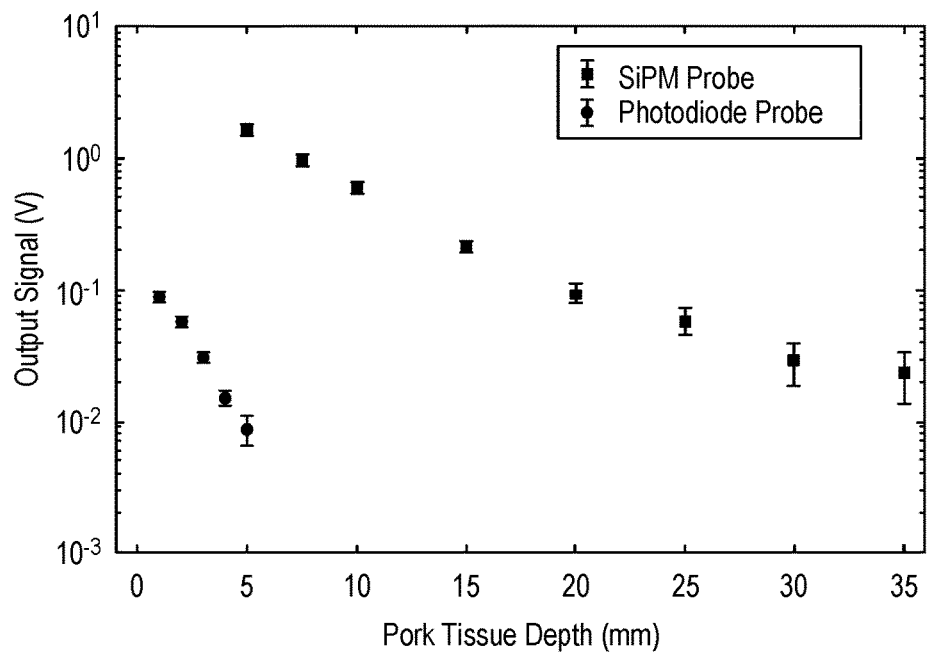
FIG. 13 is a graph showing signal strength versus the distance between the probe and the edge of a 1×3 cm 6 MV field through a ground pork phantom for both the optical probe and the silicon photodiode probe.

FIG. 13 shows output signal comparison between the SiPM probe and the silicon photodiode probe. The signals are collected under broad beam conditions, where there is no collimation. Since the ground pork is an optically scattering medium, the signal is primarily from scattered optical photons. Remarkably, the SiPM probe can detect CE optical signals from a radiation field that is seven times deeper than what the photodiode probe can detect (35 mm vs. 5 mm).

The peak of the CE is in the blue, which is outside of the biological optical window (in this case, there is strong blue absorption from the myoglobin in the ground pork). This has enormous implications for deep tissue CE measurements. The SiPM optical probe is thus an enabling step for using CE for in-vivo dosimetry by allowing for dose measurements deeper into the tissue than other optical imaging modalities.

This work has shown the feasibility of using SiPMs as effective optical sensors to detect deep tissue CE for in vivo dosimetry during EBRT. Moreover, SiPMs have shown superior performance in low light detection conditions compared to silicon photodiodes, allowing for the CE blue light to be detected at deeper locations within the tissue. While reference has been made to the application on in vivo dosimetry during EBRT, the optical probe in this disclosure is not limited to this application.

For example, the optical probe may be used for measurement of hepatic (liver) indocyanine function. In this example, indocyanine green (ICG) is injected at a given time, over time the concentration of ICG changes in the blood as it is extracted by the liver; liver function is determined by the amount of time it takes for the ICG concentration of blood to become imperceptible. The optical probe is fitted with spectral filters for both an isosbestic point in blood and the absorbance peak of ICG in blood (600 to 900 nm). A broadband lamp (with a strong signal in the NIR) is coupled into a light pipe, the light pipe is placed onto a region of interest (e.g., abdominal cavity near the liver). The multispectral optical probe is placed near a vessel of interest (deep tissue hepatic portal vein [maybe]) and the ratio between the isosbestic point of blood and ICG absorbance peak is used to determine the concentration of ICG in the blood. This is recorded over time to gather concentration measurements as a function of time of the liver. A decay exponential function is fitted; the decay constant would directly correspond to the hepatic function. Other applications for the optical probe also fall within the broader aspects of this disclosure.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A multispectral optical probe, comprising:
    a first optical bandpass filter that operates to pass Cerenkov radiation (CE) in a first range of wavelengths;
    a first silicon photomultiplier (SiPM) photodetector configured to receive radiation passed through the first optical bandpass filter and, in response thereto, generate a first optical response signal;
    a second optical bandpass filter arranged adjacent to the first optical bandpass filter and operates to pass Cerenkov radiation in a second range of wavelengths, where the first range of wavelengths differ from the second range of wavelengths; and
    a second silicon SiPM photodetector configured to receive radiation passed through the second optical bandpass filter and, in response thereto, generate a second optical response signal.

2. The optical probe of claim 1, further comprising:
    a scintillator arranged adjacent to one of the first optical bandpass filter and the second optical bandpass filter and configured to detect ionizing radiation; and
    a third SiPM photodetector configured to receive the ionizing radiation and, in response thereto, generate a radiation response signal.

3. The optical probe of claim 1 wherein the first SiPM photodetector and the second SiPM photodetector are mounted onto a flexible substrate and the first optical bandpass filter is arranged over top the first SiPM photodetector and the second optical bandpass filter is arranged over top the second SiPM photodetector.

4. The optical probe of claim 3 wherein the flexible substrate is comprised of a polymide material.

5. The optical probe of claim 3 wherein the flexible substrate is mounted onto a light-blocking pad, where the light-blocking pad is comprised of an opaque material.

6. The optical probe of claim 5 further comprising a transparent barrier disposed over top of the first optical bandpass filter and the second optical bandpass filter and coupled along periphery to the light-blocking pad, thereby encasing the first optical bandpass filter, the second optical bandpass filter, the first SiPM photodetector and the second SiPM photodetector.

7. The optical probe of claim 1 further comprising a third SiPM photodetector arranged adjacent to at least one of the first SiPM photodetector or the second SiPM photodetector, wherein the third SiPM is encased in light blocking material.

8. A multispectral optical probe, comprising:
    a first optical bandpass filter that operates to pass Cerenkov radiation (CE) in a first range of wavelengths;
    a first silicon photomultiplier (SiPM) photodetector configured to receive radiation passed through the first optical bandpass filter and, in response thereto, generate a first optical response signal;
    a second optical bandpass filter arranged adjacent to the first optical bandpass filter and operates to pass Cerenkov radiation in a second range of wavelengths, where the first range of wavelengths differ from the second range of wavelengths;
    a second silicon SiPM photodetector configured to receive radiation passed through the second optical bandpass filter and, in response thereto, generate a second optical response signal; and
    a third SiPM photodetector arranged adjacent to at least one of the first SiPM photodetector or the second SiPM photodetector and, in response to detecting radiation, generates a background signal, where the third SiPM photodetector is covered by a light-blocking material.

9. The optical probe of claim 8 configured for placement on a treatment region of a subject.

10. The optical probe of claim 8 further comprises a fourth SiPM photodetector, where the first, second, third and fourth SiPM photodetectors are arrange in a two-by-two array.

11. The optical probe of claim 8 further comprising a controller interfaced with the first SiPM photodetector, the second SiPM photodetector and the third SiPM photodetector, and operates to subtract the background signal from the first optical response signal and the second optical response signal.

12. The optical probe of claim 8 wherein the first SiPM photodetector, the second SiPM photodetector and the third SiPM photodetector are mounted onto a flexible substrate and covered by a transparent barrier, wherein the transparent barrier seals with the flexible substrate.

13. The optical probe of claim 12 wherein the flexible substrate is comprised of a material that blocks out ambient light.

14. The optical probe of claim 13 further comprises a scintillator arranged adjacent to one of the first optical bandpass filter and the second optical bandpass filter and configured to detect ionizing radiation, such that the first SiPM photodetector, the second SiPM photodetector, the third SiPM photodetector and the scintillator are arranges in a two-by-two array.

15. A radiotherapy system, comprising:
a radiation source operates to emit an ionizing radiation beam towards a region of treatment on a subject;
an optical probe configured for placement on the region of treatment, wherein the optical probe includes
a first optical bandpass filter that operates to pass Cerenkov radiation (CE) in a first range of wavelengths;
a first silicon photomultiplier (SiPM) photodetector configured to receive radiation passed through the first optical bandpass filter and, in response thereto, generate a first optical response signal;
a second optical bandpass filter arranged adjacent to the first optical bandpass filter and operates to pass Cerenkov radiation in a second range of wavelengths, where the first range of wavelengths differ from the second range of wavelengths; and
a second silicon SiPM photodetector configured to receive radiation passed through the second optical bandpass filter and, in response thereto, generate a second optical response signal; and
a computing device in data communication with the radiation source and the optical probe, wherein the computing device receives the first optical response signal and the second optical response signal and operates to adjust the ionizing radiation beam based on the first optical response signal and the second optical response signal.

16. The radiotherapy system of claim 15 wherein the optical probe further includes a third SiPM photodetector arranged adjacent to at least one of the first SiPM photodetector or the second SiPM photodetector and, in response to detecting radiation, generates a background signal, where the third SiPM photodetector is covered by a light-blocking material.

17. The radiotherapy system of claim 16 wherein the computing device is in data communication with the third SiPM photodetector and operates to subtract the background signal from the first optical response signal and the second optical response signal.

18. The radiotherapy system of claim 16 wherein the computing device adjusts intensity of the ionizing radiation beam based on the first optical response signal and the second optical response signal.

* * * * *